United States Patent [19]

Zolle

[11] Patent Number: 4,490,350
[45] Date of Patent: Dec. 25, 1984

[54] CARRIER-FREE RADIOLABELLED METYRAPONES

[76] Inventor: Llse Zolle, Zimmermanngasse 22/8, Vienna, Austria, 1090

[21] Appl. No.: 367,372

[22] Filed: Apr. 12, 1982

[51] Int. Cl.[3] ............................................. A61K 49/02
[52] U.S. Cl. ................................................... 424/1.1
[58] Field of Search .......................... 424/1, 1.5, 1.1; 546/262, 267

[56] References Cited

U.S. PATENT DOCUMENTS

| | | | |
|---|---|---|---|
| 2,923,710 | 2/1960 | Bencze et al. | 260/290 |
| 2,966,493 | 12/1960 | Allen et al. | 546/262 |
| 3,118,898 | 1/1964 | Yost | 546/262 |
| 4,051,241 | 9/1977 | Segre | 260/397.45 |

FOREIGN PATENT DOCUMENTS

| | | | |
|---|---|---|---|
| 696229 | 10/1964 | Canada | 546/262 |
| 735920 | 6/1966 | Canada | 546/262 |

OTHER PUBLICATIONS

Yellin, T. D., Steroids, vol. 20, p. 609, (1972).
Meikle, A. W., Methods in Enzymology, vol. 84, pp. 585–596, (1982), "RIA of Metyrapone Reduced Metyrapoke.
Wieland et al., J. Labelled Compd. Radiopharm., vol. 13(2), p. 229, (1977); vol. 62, p. 229 (1977).
Wieland et al., J. Nuclear Medicine, vol. 17, p. 998, (1976).
Den Hertog et al., Rec. Trav. Chim. 69, 468, 1950.
Sem. Nucl. Med 8(1), 5, 1978.

Primary Examiner—Benjamin R. Padgett
Assistant Examiner—M. Moskowitz
Attorney, Agent, or Firm—Albert F. Kronman

[57] ABSTRACT

Disclosed is the radiohalolabelling of metyrapone (1-propanone-1,2-di-(3-pyridinyl)-2-methyl), an 11Beta-hydroxylase inhibitor and of related compounds to form imaging agents for the adrenal cortex. Metyrapone was selectively converted to its mono-N-oxide. 4'-Bromo-metyrapone was obtained therefrom by a three-step conversion. Exchange labelling of the latter gave radiolabelled metyrapone. Found suitable as imaging agents are [77]Br-4-bromo-metyrapone; [131]-4-iodo-metyrapone; [123]-4-iodometyrapone and their corresponding metyrapoles. Mixtures of these also can be used as imaging agents.

8 Claims, No Drawings

CARRIER-FREE RADIOLABELLED METYRAPONES

FIELD OF THE INVENTION

This invention relates to novel adrenal scanning agents and to methods for synthesizing same.

STATEMENT OF THE PRIOR ART

Many pharmacologically active compounds that possess aniline or pyridine moieties have been shown to inhibit the adrenal cortex enzymes, 11 Beta-hydroxylase, 17α-hydroxylase and alpha 20-hydroxylase (see Sem. Nucl. Med. 8(1), 5, 1978). Wieland and Beierwaltes have studied the biodistribution of a series of known enzyme inhibitors labelled with tritium or iodine (as disclosed in J. Nucl. Med. 17 (998) 1976). Metyrapone and some analogs showed a considerable uptake in the adrenal cortex of the dog and would therefore hold the most promise for use as nuclear imaging agents.

Pyridines are highly resistant to direct halogenation. However, N-oxidation has been effectively used to introduce a number of functional groups. Nitro-N-oxides are the key intermediates in the synthetic approach to halogen derivatives. Halogenation may be accomplished via diazotization of the reduced nitro-group or directly by halogen substitution. 5'-iodo-metyrapone was described by Wieland et al—(J. Label Comp. Radiopharm 13,229 (1977)) in preference to the 4'-iodo compound. A comparison between tritiated metyrapole and 5'-iodometyrapole, however, indicated that a considerable loss of selectivity in dogs was caused by halogenation. (J. Nucl. Med. (8), 14, 1978)

SUMMARY OF THE INVENTION

The present invention resides in a novel synthesis for halogenating in the 4'-position. The advantage of this procedure is the preparation of labelled metyrapone and derivatives thereof by halogen exchange as the final reaction step. This avoids further handling of the labelled compound, which is important in the case of short-lived radionuclides.

The reactions of Scheme 1 below illustrate the invention.

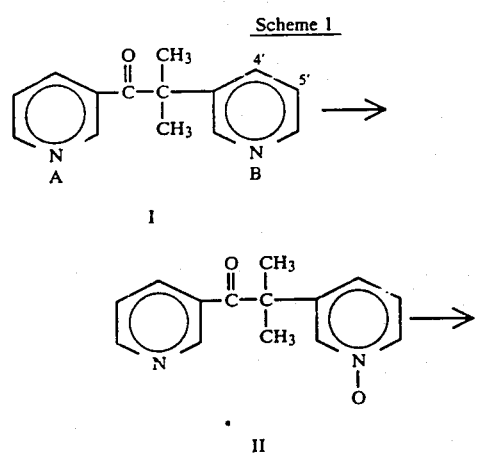

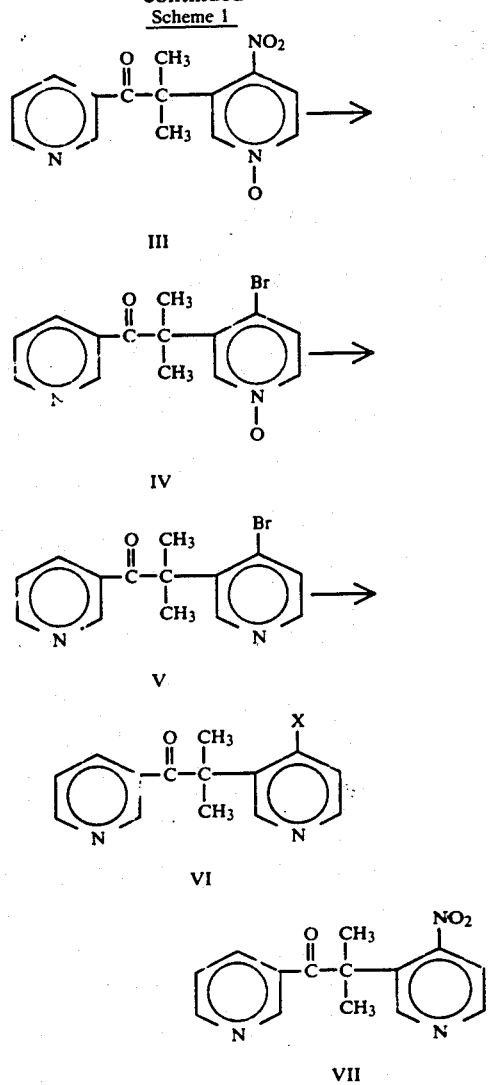

Referring to the above reactions, N-oxidation of metyrapone (I) with m-chloroperbenzoic acid leads under specified conditions to the mono-N-oxide (II) with structural evidence thereof established by $^{13}$C-NMR spectroscopy. N-oxidation of ring B causes a downfield shift of C-3', (see Table 1 below), which is easily identified in the off-resonance decoupled spectrum. The 4'nitro derivative (III) was obtained from (II) by treatment with a mixture of fuming nitric acid and sulphuric acid at 95° C. for 18 hours (as suggested by Den Hertog et al in Rec. Trav. Chim. 69,468, 1950).

In the subsequent reaction steps, 3-methyl-4-nitropyridine N-oxide was adopted as the model compound, because of its similarity with ring B of III. It was converted to 3-methyl-4-bromo-pyridine-N-oxide, respectively, 3-methyl-4-bromopyridine respectively by known reactions. Both compounds were refluxed for 24 hours with 48% HI giving 3-methyl-4-iodopyridine in good yield contaminated with only a small amount of 3-methyl-4-bromopyridine. These results showed that halogen exchange of 4-bromo substituted pyridines is independent of the N-oxide group and thus offers a simple and effective route to carrier-free 4'-iodometyrapone.

Attempts to cause displacement of the nitro group by bromine and simultaneous reduction of the N-oxide of (III) with phosphorus tribromide failed to produce halogenation and yielded 4'-nitro-metyrapone (VII) only. In an alternate attempt, 4'nitrometyrapone-N-oxide (III) was treated with acetyl bromide at 75° C. for 1 hour cleanly affording 4'-bromo-metyrapone-N-oxide (IV). Catalytic hydrogenation of (IV) with Raney-Nickel W-2 is ethanol gave 4'-bromo-metyrapone (V) suitable for exchange labelling with $Na^{131}I$, $Na^{123}I$ and $Na^{77}Br$ to form (VI), wherein X is $^{131}I$, $^{123}I$ or $^{77}Br$.

The invention is illustrated in non-limiting fashion by the following examples:

NMR spectra were determined for approx. 0.05M ($^1H$) respectively 0.4–0.6M ($^{13}C$) solutions in $CDCl_3$ with tetramethylsilane as the internal standard on a Bruker WM-250 spectrometer.

Typical parameters: $^1H$: SF-250.132 MHz, PW=1 μs (15°), SW=2500 Hz, digital resolutions: 0.3 Hz $^{13}C$: SF-62.89 MHz, PW-6 μs (35°) SW-15000 Hz, digital resolutions: 0.9 Hz. The mass spectra were determined on a Varian MAT CH-7 spectrometer. Analytical TLC: Merck Silica Gel F 254 in two solvent systems. The melting points are uncorrected. High specific activity iodide was used: $Na^{131}I$: Amersham—18S 500, $Na^{123}I$: Belgium/Switzerland 1A-21.

EXAMPLE 1

This example shows the synthesis of 1-Propanone-1-(3-pyridinyl)-2-(3-pyridinyl-1-oxide)-2-methyl (Metyrapone-N-oxide, II).

A cooled solution (0° C.) of m-chloroperbenzoic acid (6.7 g, 85%) in $CHCl_3$ (80 ml) was added to a solution of metyrapone (5 g) in $CHCl_3$ (40 ml) at 0° C. during 2 hours. The mixture was stirred for a further 4 hours at 0° C. The organic phase was then washed twice with saturated aqueous sodium bicarbonate (200 ml) and once with water (150 ml). Evaporation of the dried ($Na_2SO_4$) chloroform phase yielded a crystalline residue, which on recrystallization from ethyl acetate gave 3.8 g of II (71%). mp. 165°–167° C. (lit[10] mp. 144°–150° C.).

$^1H$-NMR: σ (ppm) 1.60(H-9), 7.12(H-4'), 7.27(H-5'), 7.30(H-5), 7.86(H-4), 8.15(H-6'), 8.30(H-2'), 8.66(H-6), 8.77(H-2). Anal. Calcd. for $C_{14}H_{14}N_2O_2$; C, 69.40; H, 5.82; N, 11.56. Found: C, 69.24; H, 5.77; N, 11.54.

EXAMPLE 2

Preparation of 1-Propanone-1-(3-pyridinyl)-2-(4-nitro-3-pyridinyl-1-oxide)-2-methyl; 4'-Nitro metyrapone-N-oxide(III)

The N-oxide II prepared in the previous example (2.75 g) was dissolved in concentrated sulphuric acid (7 ml) at 0° C. and added dropwise to a stirred mixture of fuming nitric acid (12 ml) and concentrated sulphuric acid (7 ml). The mixture was stirred at room temperature for 1 hour and then heated to 95° C. for 18 hours. After cooling, water (80 ml) was added, keeping the vessel in an ice bath. The pH of the solution was adjusted to 5.3 by addition of 6N NaOH. The product was extracted with chloroform (6×50 ml). The organic layer was dried over $Na_2SO_4$ and evaporated. The residue was recrystallized from ethyl acetate giving 1.65 g (51%) of (III) as yellow needles.

mp. 169°–172° C., $^1H$-NMR: 6(ppm): 1.82 (H-9), 7.36 (H-5'), 8.00 (H-5'), 8.04 (H-4), 8.19 (H-6'), 8.53 (H-2'), 8.68 (H-6), 8.79 (H-2);

Anal. Calcd. for $C_{14}H_{13}N_3O_4$: C, 58.53; H, 4.56; N, 14.63. Found: C, 58.37; H, 4.55; N, 14.35.

EXAMPLE 3

Preparation of 1-Propanone-1-(3-pyridinyl)-2-(4-bromo-3-pyridinyl-1-oxide)-2-methyl;4'-bromometyrapone-N-oxide (IV)

The nitro-N-oxide prepared in the previous example (III),(1.6 g) was added in small portions to ice-cooled acetyl bromide (12 ml). The resulting suspension was stirred for 30 min at 0° C. and for an additional 30 min at room temperature followed by heating at 75° for 45 min. The cooled mixture was poured onto crushed ice (100 g), the aqueous phase made alkaline with $K_2CO_3$ and the product was extracted with $CHCl_3$ (3×50 ml). The dried ($K_2CO_3$) solvent was evaporated and the product was purified as above giving 1.2 g (67%) of (IV) mp. 185°–187° C., $^1H$-NMR: 6(ppm): 1.78(H-9), 7.29(H-5), 7.33(H-5'), 7.97(H-4), 7.99(H-6'), 8.52(H-2'), 8.69(H-6), 8.88(H-2).

Anal Calcd. for $C_{14}H_{13}BrN_2O_2$: C, 52.35; H, 4.08; Br, 24.88; N, 8.72. Found: C, 52.03; H, 4.06; Br, 24.49; N, 8.67.

EXAMPLE 4

Preparation of 1-Propanone-1-(3-pyridinyl)-2-(4-bromo-3-pyridinyl)-2-methyl;4'-bromometyrapone (V)

A solution of the bromo-N-oxide IV" prepared in the above example (2 g) in ethanol (200 ml) was stirred with Raney-Nickel W-2 (400 mg) under hydrogen for 6 hours. After filtration and evaporation, the residual oil was distilled (150° C./0.001 Torr) giving a crystalline product. Further purification was carried out by recrystallization (ethyl acetate) yielding 1.46 g of V (77%). mp. 89°–90° C., $^1H$-NMR: σ (ppm): 1.83(H-9), 7.22(H-5), 7.40(H-5'), 7.95(H-4), 8.36(H-6'), 8.61(H-6), 8.80(H-2), 8.91(H-2'), mass spectrum: m/e: 304/306(M+), 198/200, 170/172, 106, 78 Anal. Calcd. for $C_{14}H_{13}BrN_2O$: C, 55.10; H, 4.29; Br, 26.19; N, 9.18; Found: C, 54.97; H, 4.20; Br, 26.00; N, 9.09.

EXAMPLE 5

This example shows the exchange labelling of (V):

To a solution of 4'-bromometyrapone (1.5 mg) in ethanol (0.05 ml) a solution of $Na^{131}I$ (1.5 mCi) in ethanol (0.1 ml) was added. $Na_2S_2O_5$ (20 μg) was added as an aqueous solution (0.005 ml). The solvent was evaporated to dryness (vacuum) and the reaction mixture was heated for 2 hours at 168° C. After cooling, the reaction product was dissolved in $CHCl_3$ (1 ml) and separated from free radioiodide by Cellex D column filtration.

After evaporation of $CHCl_3$, the product was dissolved in ethanol and used for injection as 5–10% ethanol solution in saline. Radiochemical yield: 75–80% of VI. Radiochemical purity: TLC revealed one distinct radioactive spot identical with the 4'-bromo-metyrapone standard and no free iodide.

EXAMPLE 6

Preparation of 1-Propanone-1-(3-pyridinyl)-2-(4-nitro-3-pyridinyl)-2-methyl 4-nitrometyrapone (VII)

A solution of $PBr_3$ (0.8 ml) in $CHCl_3$ (3 ml) was added to a cooled solution of the nitro-N-oxide III (0.5 g) in $CHCl_3$ (10 ml). The mixture was refluxed for 3 hours.

cooled, poured onto ice and made alkaline by addition of K₂CO₃. The product was extracted with CHCl₃ (3×25 ml); the dried solvent (Na₂SO₄) evaporated and the product distilled 103° C./ 0.001 Torr) yielding 0.3 g (64%) of (VII) as a colorless oil. $^1$H-NMR: σ (ppm): 1.86(H-9), 7.32(H-5), 7.66(H-5'), 8.00(H-4), 8.66(H-6), 8.76(H-2), 8.86(H-6'), 9.16(H-2').

Anal. Calcd. for $C_{14}H_{13}N_3O_3$: C, 61.98; H, 4.83; N, 15.49. Found: C, 61.66; H, 4.84; N, 15.26.

EXAMPLE 7

This example shows the exchange labelling of the previously made compounds.

$^{131}$I and $^{123}$I was introduced in the above compound in the molten state as described previously in Int. J. Appl. Radiat. isotopes, 24,463 (1973).

4'-Bromo-metyrapone is highly resistant to heating, showing no degradation products by TLC. The influence of temperature on the radiochemical yield was stuided over a range of 120°–168° C. Maximum incorporation (75–80%) was measured between 165°–168° C. after 2 hours of heating; at 1 hour the exchange was between 55–60%. Incorporation was independent of the amount of V (1–10 mg) and radioactivity (0.001–1.5 mCi) used. During the initial evaporation of solvent varying amounts of radioactivity may be lost. This loss was eliminated by the addition of sodium thiosulfate, or preferably of sodium metabisulfite, which did not interfere with subsequent labelling.

Free iodide was separated from the product by Cellex D column filtration or extraction with an alkaline aqueous solution. In the first case, the labelled compound is dissolved in chloroform (0.5 ml) and placed onto a Cellex D column (in a 2 ml syringe suspended in ethanol) and eluted with approx. 2 ml chloroform which contains the labelled material and no free iodide. In the case of extraction, the labelled compound is dissolved in chloroform (0.5–1.0 ml) to which is added an equal volume of a solution containing 0.5 mg potassium iodide, 0.5 mg sodium thiosulfate and 1 mg potassium carbonate. Extraction is performed twice and the organic phase washed once with water. The chloroform is evaporated and the dry material is dissolved in ethanol (0.1–0.2 ml) and then further diluted with saline to 2 ml. (after steril filtration through a membrane filter (0.22 um), the labelled compound is ready for intravenous injection in man.

TABLE I $^{13}$C—shifts of 4'-substituted metyrapones (ppm, internal TMS, 0.4–0.6M in CDCl₃)

| Compound | (1) | (2) | (3) | (4) | (5) |
|---|---|---|---|---|---|
| R₁ | — | 0 | 0 | 0 | — |
| R₂ | H | H | NO₂ | Br | Br |
| Carbon | | | | | |
| 6' | 148.6 | 137.9 | 138.3 | 138.6 | 149.4 |
| 5' | 123.8 | 126.2 | 123.3 | 131.5 | 129.3 |
| 4' | 133.5 | 123.3 | 142.0 | 119.1 | 133.6 |

TABLE I-continued $^{13}$C—shifts of 4'-substituted metyrapones (ppm, internal TMS, 0.4–0.6M in CDCl₃)

| Compound | (1) | (2) | (3) | (4) | (5) |
|---|---|---|---|---|---|
| 3' | 139.9 | 144.3 | 139.9 | 144.1 | 140.2 |
| 2' | 147.9 | 137.4 | 139.6 | 138.5 | 148.3 |
| 8 | 50.5 | 50.3 | 50.9 | 52.0 | 51.8 |
| 9 | 27.3 | 26.9 | 27.2 | 26.4 | 26.6 |
| 7 | 201.3 | 200.0 | 198.5 | 199.1 | 200.3 |
| 2 | 150.7 | 150.4 | 149.2 | 150.1 | 150.1 |
| 3 | 131.6 | 131.1 | 132.2 | 131.4 | 131.2 |
| 4 | 136.6 | 136.5 | 136.3 | 136.1 | 136.3 |
| 5 | 123.0 | 123.2 | 123.5 | 123.2 | 123.0 |
| 6 | 152.2 | 152.6 | 152.5 | 152.8 | 152.4 |

EXAMPLE 8

The metyrapoles corresponding to the above metyrapones are prepared by treating the latter with a reducing agent such as LiAlH₄ or LiAlH(p-t-Bu)₃ to convert the beta group to hydroxyl as follows:

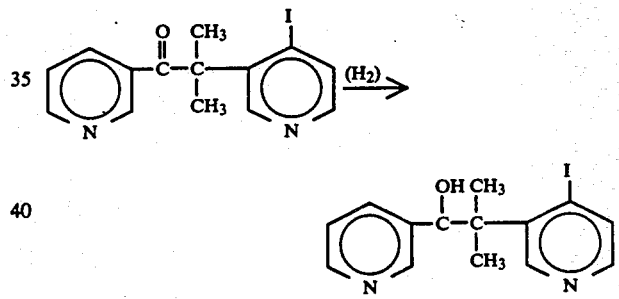

Mixtures of radiolabelled metyrapoles and metyrapones can be used as scanning agents. $^{123}$I-labelled metyrapole and metyrapone are particularly useful as imaging agents of the adrenal gland for the diagnosis of hyperplasia or adenoma. 1.5 to 2.0 mCi of labelled compound are required for adequate imaging of the gland. They are used in a 5% ethanol solution in saline.

Tables II and III show data for the biodistribution of $^{131}$I-iodometyrapone which were obtained in rats and two dogs. For comparison Wielands data, from J. Nucl. Med. 17,998 (1976), are given in the last column on the right. Blanks mean that no value has been reported for the organ. These tables show that the results compare with the above data.

Advantageously, the labelled iodo- and bromometyrapones can be obtained in the carrier-free state in the sense that no cold or unlabelled metyrapone is in the final product, which would actually dilute the radioactively labelled metyrapone. However, minor amounts of unreacted Br-metyrapone may also be considered a carrier for the labelled product. The unreacted Br-metyrapone can be separated from labelled product by HPLC (high pressure liquid chromatography), to obtain the carrier-free product.

TABLE II

RELATIVE TISSUE DISTRIBUTION of $^{131}$I—IODOMETYRAPONE in RATS at DIFFERENT TIMES after INJECTION
(% kg dose/g tissue; mean ± s.e.m.)

| Organ | Time (min) 10 | 30 | 60 | 120 | Wieland 1976 $^3$H—metyrapone 10 min |
|---|---|---|---|---|---|
| Heart | 0.11 ± 0.01 | 0.11 ± 0.01 | 0.09 ± 0.01 | 0.04 ± 0.01 | — |
| Lung | 0.19 ± 0.07 | 0.31 ± 0.26 | 0.19 ± 0.02 | 0.14 ± 0.02 | — |
| Liver | 0.30 ± 0.08 | 0.31 ± 0.02 | 0.17 ± 0.03 | 0.10 ± 0.01 | 0.27 |
| Spleen | 0.12 ± 0.01 | 0.12 ± 0.01 | 0.10 ± 0.01 | 0.05 ± 0.01 | — |
| Stomach | 0.42 ± 0.10 | 0.49 ± 0.07 | 0.46 ± 0.11 | 0.51 ± 0.06 | — |
| Ovary | 0.18 ± 0.03 | 0.17 ± 0.02 | 0.14 ± 0.03 | 0.07 ± 0.01 | 0.08 |
| Kidney | 0.17 ± 0.01 | 0.21 ± 0.02 | 0.16 ± 0.02 | 0.10 ± 0.02 | 0.16 |
| Adrenal | 0.91 ± 0.30 | 0.79 ± 0.22 | 0.50 ± 0.15 | 0.21 ± 0.03 | 0.94 |
| Thyroid | 0.51 ± 0.33 | 0.38 ± 0.05 | 2.29 ± 0.15 | 4.02 ± 1.45 | 0.05 |
|  | X = 8 | X = 4 | X = 4 | X = 5 |  |

TABLE III

RELATIVE TISSUE DISTRIBUTION OF $^{131}$I—IODOMETYRAPONE in DOGS 30 min after INJECTION

| Organ | % of injected $^{131}$I/organ | % kg dose/g tissue | Wieland 1976 $^3$H—metyrapone at 45 min |
|---|---|---|---|
| Heart | 0.98 | 0.10 | — |
| Lung | 3.18 | 0.20 | — |
| Liver + Bile | 20.2 | 1.02 | 0.44 |
| Spleen | 0.83 | 0.12 | — |
| Jejunum | 0.26 | 0.21 | — |
| Pancreas | 0.07 | 0.05 | — |
| Ovary | 0.02 | 0.15 | 0.10 |
| Kidney | 3.90 | 0.65 | 0.28 |
| Adrenal | 0.20 | 2.50 | 2.75 |
| Thyroid | 0.03 | 0.13 | 0.07 |
| Blood | 11.92 | 0.13 | 0.17 |
| Urine | 0.17 | 0.12 | 31.30 |

What is claimed is:

1. An adrenal scanning agent selected from the group consisting of:
   $^{77}$Br-4-bromo-metyrapone
   $^{131}$I-4-iodo-metyrapone
   $^{123}$I-4-iodo-metyrapone
   $^{77}$Br-4-bromo-metyrapole
   $^{131}$I-4-iodo-metyrapole
   $^{123}$I-4-iodo-metyrapole
   and mixtures thereof.

2. An agent according to claim 1, containing also a minor amount of 4'bromo-metyrapone as a carrier.

3. A process for making an adrenal scanning agent comprising the steps of:
   converting metyrapone to its mono-N-oxide;
   converting the resulting metyrapone mono-N-oxide to 4'-bromo-metyrapone;
   exchange labelling 4'-bromo-metyrapone with Na$^{131}$I, Na$^{77}$Br or Na$^{123}$I, to form the corresponding 4-radiolabelled metyrapone.

4. The process of claim 3, wherein the 4-radiolabelled metyrapone is treated with a reducing agent to form the corresponding 4-radiolabelled metyrapole.

5. The process of claims 3, wherein said exchange labelling is carried out in the presence of sodium thiosulfate or sodium metabisulfite to prevent loss of radioactivity during labelling.

6. The process of claims 3, wherein unreacted 4' bromo-metyrapone is separated from the 4-radiolabelled metyrapone to form a substantially carrier-free product.

7. The process of claim 3, wherein said exchange labelling is effected by heating (with $^{131}$I or $^{123}$I) said 4'-bromo-metyrapone in the molten state with radiohalogen at 120° to 168° C., (the ratioactivity ranging from 0.001 to 1.5 mci) for about two hours.

8. The process of claim 7, wherein said heating is effected with $^{131}$I or $^{123}$I at 165° to 168°.